United States Patent
Lee

(10) Patent No.: US 9,157,068 B2
(45) Date of Patent: *Oct. 13, 2015

(54) FORMULATION FOR CULTIVATING DENDRITIC KILLER CELLS AND METHOD USING THE SAME

(71) Applicant: FullHope Biomedical Co., Ltd., Taipei (TW)

(72) Inventor: Jan-Mou Lee, Taipei (TW)

(73) Assignee: FULLHOPE BIOMEDICAL CO., LTD., Taipei (TW)

( * ) Notice: Subject to any disclaimer, the term of this patent is extended or adjusted under 35 U.S.C. 154(b) by 137 days.

This patent is subject to a terminal disclaimer.

(21) Appl. No.: 13/918,718

(22) Filed: Jun. 14, 2013

(65) Prior Publication Data

US 2014/0011276 A1    Jan. 9, 2014

(30) Foreign Application Priority Data

Jul. 5, 2012   (TW) .............................. 101124294 A

(51) Int. Cl.
*C12N 5/00* (2006.01)
*C12N 5/02* (2006.01)
*C12N 5/0784* (2010.01)

(52) U.S. Cl.
CPC ...... *C12N 5/0639* (2013.01); *C12N 2501/2315* (2013.01)

(58) Field of Classification Search
None
See application file for complete search history.

(56) References Cited

PUBLICATIONS

Lin et al., 2004, Ped. Aller. Immunol. vol. 15: 79-85 Tortorella et al., 2002, Mech. Age. Devel. vol. 123: 1389-1402.*
Lin et al., 1998, J. Clin. Immunol. vol. 18: 335-345.*
Seidel et al., 1998, Naunyn-Schmeid. Arch. Pharm. vol. 358: 382-389.*
Freshney, 2006, Cultures of Tissue Engineer. pp. 3-22.*

* cited by examiner

*Primary Examiner* — Amy Juedes
(74) *Attorney, Agent, or Firm* — WPAT, PC; Justin King

(57) ABSTRACT

A formulation and method for cultivating dendritic killer cells is disclosed in the present invention. The formulation comprises an effective amount of at least one cytokine and the abovementioned cytokine is IL-15. Furthermore, the method for cultivating dendritic killer cells at least comprises the following steps. A peripheral blood mononuclear cell population is obtained from human blood at first. Effective amounts of the cytokines in the formulation mentioned above are then added into the peripheral blood mononuclear cell population and the abovementioned peripheral blood mononuclear cell population is placed for a first appropriate period.

11 Claims, 8 Drawing Sheets

FORMULATION FOR CULTIVATING DENDRITIC KILLER CELLS AND METHOD USING THE SAME

CROSS-REFERENCE TO RELATED APPLICATIONS

This Non-provisional application claims priority under 35 U.S.C. §119(a) on Patent Application No(s). 101124294 filed in Taiwan, Republic of China, 07, 05, 2012, the entire contents of which are hereby incorporated by reference.

FIELD OF THE INVENTION

This invention relates to a formulation for cultivating dendritic killer cells and a method using the same, especially relates to a formulation for bulkily generating dendritic killer cells ex vivo by utilizing IL-15 and a method using the same.

BACKGROUND OF THE INVENTION

Human body will recognize the extraneous matter and start a series of defending process. This defense system is named as immune system. There are many different cells such as leukocytes and lymphocyte, and different protein factors such as immunoglobulins and cytokines working coordinately to protect the body. The immune systems are traditionally divided into innate and adaptive immune systems. Innate immune system is including soluble complement system, polymorphonuclear neutrophils, macrophages and natural killer cells. Adaptive immune system is including humoral and cellular immunity. Humoral immunity as well as cellular immunity involves lymphocyte, lymphokine and immunological memory system. The long-lasting immune memory mounts quick and strong immune responses towards the same pathogen which has invaded the body.

Immune system may respond to different pathogens due to the diversity of major histocompatibility complex (MHC) molecules. The endogenous and exogenous antigens derived from pathogens, are assembled with MHC molecules on the surface of antigen-presenting cells (APC) and then presented to T cells expressing corresponding T cell receptors. MHC in the human beings can be called Human Leukocyte Antigen, HLA, which can be categorized into class I, class II, and class III. HLA class I is widely expressed on all the somatic cells but Class II distribution is restricted to macrophages, B cells and dendritic cells.

Dendritic cells (DC), which have the broadest range of antigen presentation, are professional APC, and named by the appearance of dendrites extending from the cell body. DCs reside in the periphery of body as immature DCs (imDCs). Once pathogen invades human bodies, imDCs capture pathogen-derived antigens, migrate to draining lymph nodes to become mature DCs (mDCs), and present antigens to corresponding T cells there. Therefore, dendritic cells are the starter of the pathogen-specific cellular immune responses.

Natural killer (NK) cells, a key player of innate immune system, spontaneously kill tumor or virally infected cells prior to activation. Mechanisms underlying cytotoxicity of NK cells are grouped into two parts: a) interaction of cell surface tumor necrosis factor superfamily members and their receptors which leads to apoptosis of target cells, (b) release of soluble perforin and granzymes. NK cells are rich with small granules in their cytoplasm contain special proteins such as perforin and proteases known as granzymes. Upon release in close proximity to a cell slated for killing, perforin forms pores in the cell membrane of the target cell through which the granzymes and associated molecules can diffuse in, leading to destruction of target cells. Once virally infected cells or tumor cells have been killed, viral genomic content (CpG or poly I:C), cellular metabolites, and bystander cytokines such as IFN-γ, IL-12 and TNF-α would further activate and augment NK cell activity in term of cytotoxicity and effector cytokine production. Therefore NK cells serve as key innate effector cells targeting to virally infected cells and tumor cells in a non-antigen specific manner while DCs in adaptive immune system trigger antigen-specific cytotoxic T cells which can further clear the infection. Patients deficient in NK cells are proved to be highly susceptible to early phases of herpes virus infection. Interferon-producing killer dendritic cells (IKDCs), a recently identified leukocyte population in mice, express phenotypes of non-T (CD3$^-$), non-B (CD19$^-$), intermediate levels of CD11c, and high levels of B220 and NK-specific markers, including NK1.1, DX5, NKG2D and Ly49 family receptors. IKDCs functionally resemble NK cells in cytotoxicity against tumor cells and in production of abundant IFN-γ. On the other hand, upon stimulation with CpG or tumor cells, IKDCs down-regulate NKG2D, up-regulate MHC II, and acquire moderate APC-like activity that activates antigen-specific T cells. Despite acquisition of APC activity after certain stimulations, IKDCs appear to belong to the NK lineage rather than DC lineage. IKDCs express NK-specific Ner-1 transcripts (encoding NKp46) but not PU.1 that is predominantly expressed in DCs and plasmacytoid DCs. Furthermore, IKDC development parallels NK cells in their strict dependence on the IL-15 cytokine system. Therefore, the putative IKDCs are functionally and developmentally similar to NK cells. Although debates regarding tumoricidal activity and cell lineage development of IKDC were raised herein, further investigations were limited by rare abundance of IKDC in periphery. The frequency of IKDCs in a mouse spleen is below 0.01%, and is even lower in the lymph nodes. Therefore, cumbersome procedure is required for the purification of IKDCs, and the yield is low. This problem has limited the use of IKDCs in research and in application.

SUMMARY OF THE INVENTION

According to the abovementioned disadvantages of the prior art, Applicant put a lot of efforts in the past years and successfully screens out cells which have the functions of both natural killer cells and dendritic Cells. The abovementioned cells are defined as Dendritic killer cell (hereafter called DKC), also be called cytotoxic dendritic cell (cytoDC). However, it is noted that the DKC constitutes less than 0.01% of peripheral lymphocytes. Please refer to FIG. 1 and FIGS. 2A to 2B. FIG. 1 is diagram showing the percentage of DKC in human peripheral blood of the cancer patient and the healthy donor. FIG. 2A is diagram showing the result of using a flow cytometer to analyze human peripheral blood of a cancer patient in the preferred embodiment of the present invention, and FIG. 2B is diagram showing the result of using a flow cytometer to analyze human peripheral blood of a healthy donor in the preferred embodiment of the present invention. As shown in FIG. 1, the percentage of the DKC in human peripheral blood of the cancer patient is obviously lower than that of the healthy donor. Furthermore, as shown in the upper right corner of FIG. 2A, it is noted that the percentage of the DKC 10 in the human peripheral blood of the cancer patient is only 0.0367%. However, as shown in the upper right corner of FIG. 2B, the percentage of the DKC 10 in the human peripheral blood of the healthy donor is 0.436%.

That is, the counts of the DKC which are existed in the human peripheral blood of the healthy donor are higher than that of the cancer patient.

Therefore, Applicant further provides a formulation and a method for cultivating dendritic killer cells. The present invention successfully makes trace DKC of human blood increase in an amount of 200-fold to 400-fold, and is expected to develop cell immunotherapy of cancer.

According to the abovementioned, the present invention provides a formulation for cultivating DKC. The formulation comprises an effective amount of at least one cytokine, and the cytokine mentioned as above is IL-15.

Preferably, the concentration of IL-15 has a value greater than 1 ng/mL.

Preferably, the concentration of IL-15 has a value of 10 ng/mL.

Preferably, the formulation further comprises an effective amount of another cytokine, and another cytokine mentioned as above is IL-12. Preferably, the concentration of IL-12 has a value between 0.5~20 ng/mL. Furthermore, the formulation disclosed in the present invention will make the DKC of human blood increase in an amount of 200-fold to 400-fold. Preferably, the human blood is collected from a cancer patient.

The present invention further provides a method for cultivating DKC, and the method comprises the following steps. First, a peripheral blood mononuclear cell population is obtained from human blood at first. And then, the step of adding an effective amount of a formulation to mix with the peripheral blood mononuclear cell population is performed. Preferably, the formulation comprises at least one cytokine and the cytokine is IL-15. The following step is to place the peripheral blood mononuclear cell population for a first appropriate period.

Preferably, the formulation further comprises an effective amount of another cytokine, and another cytokine mentioned as above is IL-12. Preferably, the concentration of IL-15 has a value greater than ing/mL. Preferably, the concentration of IL-15 has a value has a value of 10 ng/mL, and the concentration of IL-12 has a value between 0.5~20 ng/mL.

Preferably, the method disclosed in the present invention further comprises the following steps. First, the step of collecting non-adherent cells is performed. A first precipitation is obtained by treating the non-adherent cells. The first precipitation will be re-suspended by using the abovementioned formulation. The following step of placing the re-suspended first precipitation for a second appropriate period is then performed.

Preferably, after the step of placing the peripheral blood mononuclear cell population for the first appropriate period or placing the re-suspended first precipitation for the second appropriate period, the method further comprises the following step of sorting a dendritic killer cell population. It is noted that the cell counts of the sorted dendritic killer cell population have a 200-fold to 400-fold higher value than that of human blood. Furthermore, the abovementioned sorting step is performed by a flow cytometer or other related technology. However, the present invention is not limited thereto.

Preferably, the step of obtaining the peripheral blood mononuclear cell population from the human blood further comprises the following steps. The human blood is collected at first. The peripheral blood mononuclear cell population is then sorted from the human blood. The eventual step is to remove T cells and B cells from the peripheral blood mononuclear cell population.

Preferably, the step of collecting the human blood is performed from a cancer patient. And further, a cancer, which the cancer patient suffers from, can be selected from a group consisting of squamous cell carcinoma, lobular carcinoma in situ, liver cancer, nasopharyngeal carcinoma, lung cancer, bone cancer, pancreatic cancer, skin cancer, head and neck cancers, malignant melanoma, cervical cancer, ovarian cancer, colon cancer, anal cancer, stomach cancer, breast cancer, testicular cancer, fallopian tube cancer, endometrial cancer, cervical cancer, vaginal cancer, vulvar cancer, non-Hodgkin lymphoma, Hodgkin lymphoma, esophageal cancer, thyroid cancer, adrenal cancer, cancers of mesothelial and soft tissue, urethra cancer, cancer of penis, prostate cancer, acute leukemia, chronic leukemia, lymphomas, bladder cancer, ureteral cancer, renal cell carcinoma, urothelial carcinoma, cancer of central nervous system, primary central nervous system lymphoma, glioma, pituitary tumor, Kaposi's sarcoma, squamous cell cancer and their metastasis.

The present invention further provides a method of obtaining an enriched population of human DKCs, the method comprises: First, the step of obtaining human peripheral blood mononuclear cells (PBMCs) is performed. Next, culture the human CD3$^-$CD19$^-$PBMCs in a media containing IL-15 to allow enrichment of human DKCs, wherein the DKCs are HLA-G$^-$ CD14$^-$ CD19$^-$ CD3$^-$ CD56$^+$ HLA-DR$^+$. Then, isolate non-adherent cells to obtain an enriched population of DKCs. Preferably, the media further contains IL-12. Preferably, the human peripheral blood is collected from a cancer patient.

The features and advantages of the present invention will be understood and illustrated in the following specification and FIGS. 3~7.

DETAILED DESCRIPTION OF THE INVENTION

Figure 1:
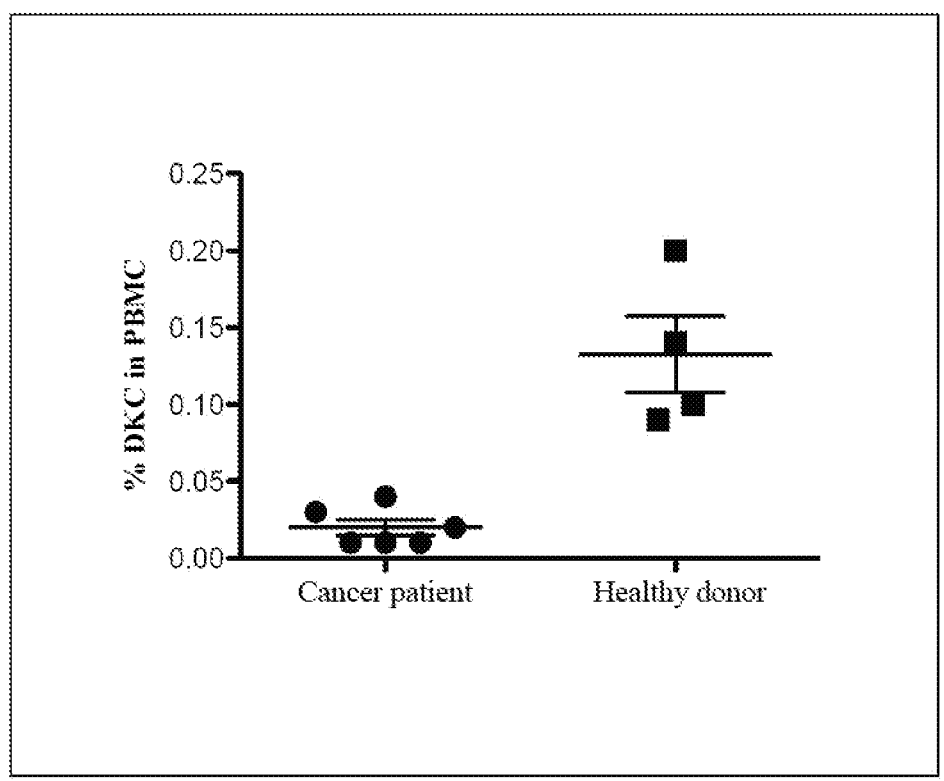
FIG. 1 is diagram showing the percentage of DKC in human peripheral blood of the cancer patient and the healthy donor.
Figure 2A:
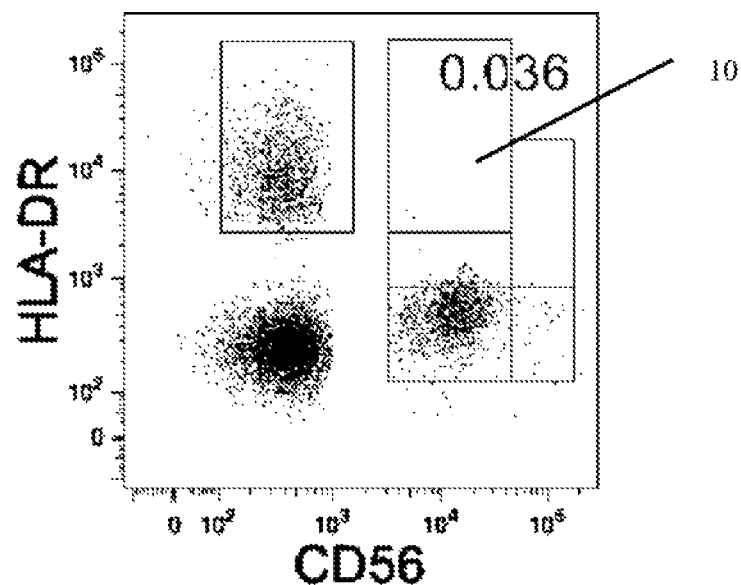
FIG. 2A is diagram showing the result of using a flow cytometer to analyze human peripheral blood of a cancer patient in the preferred embodiment of the present invention.
Figure 2B:
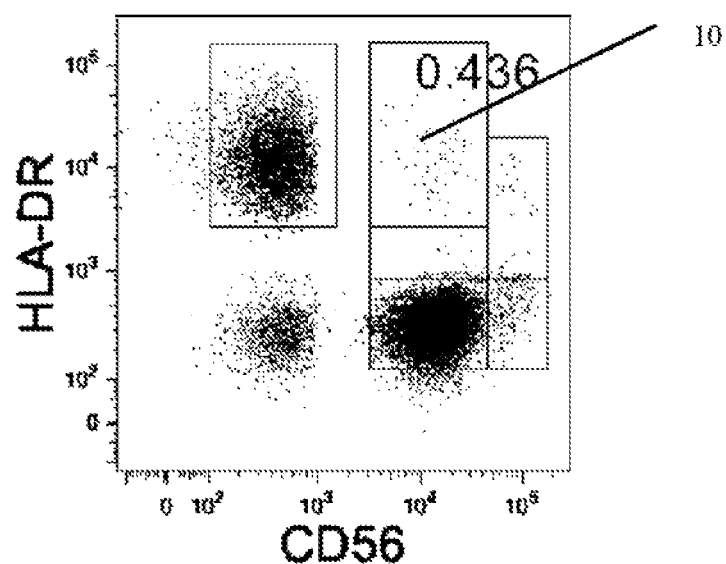
FIG. 2B is diagram showing the result of using a flow cytometer to analyze human peripheral blood of a healthy donor in the preferred embodiment of the present invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

As used herein, the term "Dendritic killer cells" or "DKC" is intended to refer to the cells with both cytotoxicity and antigen presenting cell (APC) activity.

As used herein, the symbol "+" means that the cell surface marker expresses on the surface of the cells and has a larger expressed amount measured by flow cytometer than that of the negative control.

As used herein, the symbol "−" means that the cell surface marker does not express on the surface of the cells and has an expressed amount equal to that of the negative control.

Preferably, all abovementioned expressed amount of the cell surface markers are measured by flow cytometer, however, the present invention is not limited thereto.

As used herein, the term "Interleukin" means a group of cytokines that were first seen to be expressed by white blood cells (leukocytes). It has since been found that interleukins are produced by a wide variety of body cells. The function of the immune system depends in a large part on interleukins.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

At first Applicant put a lot of efforts in the past years and successfully screens out cells which have the functions of both natural killer cells and dendritic Cells. These cells are defined as dendritic killer cell (hereafter called DKC) as mentioned above and have surface markers of $CD14^-HLA\text{-}G^-CD3^-CD19^-HLA\text{-}DR^+CD56^+$. Furthermore, the method disclosed in the present invention for cultivating dendritic killer cells is processed ex vivo.

Preferably, human blood used in the present invention is collected from a cancer patient. And further, a cancer, which the cancer patient suffers from, can be selected from a group consisting of squamous cell carcinoma, lobular carcinoma in situ, liver cancer, nasopharyngeal carcinoma, lung cancer, bone cancer, pancreatic cancer, skin cancer, head and neck cancers, malignant melanoma, cervical cancer, ovarian cancer, colon cancer, anal cancer, stomach cancer, breast cancer, testicular cancer, fallopian tube cancer, endometrial cancer, cervical cancer, vaginal cancer, vulvar cancer, non-Hodgkin lymphoma. Hodgkin lymphoma, esophageal cancer, thyroid cancer, adrenal cancer, cancers of mesothelial and soft tissue, urethra cancer, cancer of penis, prostate cancer, acute leukemia, chronic leukemia, lymphomas, bladder cancer, ureteral cancer, renal cell carcinoma, urothelial carcinoma, cancer of central nervous system, primary central nervous system lymphoma, glioma, pituitary tumor, Kaposi's sarcoma, squamous cell cancer and their metastasis.

Preferably, several sorting or screening steps are performed by a flow cytometer, and a target cell population will be screened out by utilizing at least one flow cytometer to identify different surface markers of different cells. Flow cytometry allows for single cell analysis at speeds far surpassing any other single cell analysis technology in the art. This enables a statistically significant number of cells to be analyzed faster than using other alternative techniques. In a preferred embodiment, a flow cytometer is used with any suitable sample preparation robot or liquid handler that is known in the art. Furthermore, a single laser flow cytometer is used in an embodiment for the analyzing step. In another embodiment, a multi-laser flow cytometer is used for the analyzing step and the present invention is not limited thereto.

Preferably, the development and optimization of an extensive set of fluorochromes and conjugating chemistries allows for a variety of ligands, such as immunoglobulins and small molecules, to be conjugated to the fluorochromes. Lasers with emission lines ranging from the ultraviolet to the red region of the light spectrum can excite these fluorochromes. Consequently, a large number of spectrally distinct reagents can be used to label cells for study with fluorescence-based instrumentation such as flow cytometry used in the present invention. These reagents are well known in the art. In one embodiment, one or more fluorochromes are used during the analyzing step. In some embodiments, one or more stains are used in the analysis of cellular responses to drug compositions.

Figure 3:
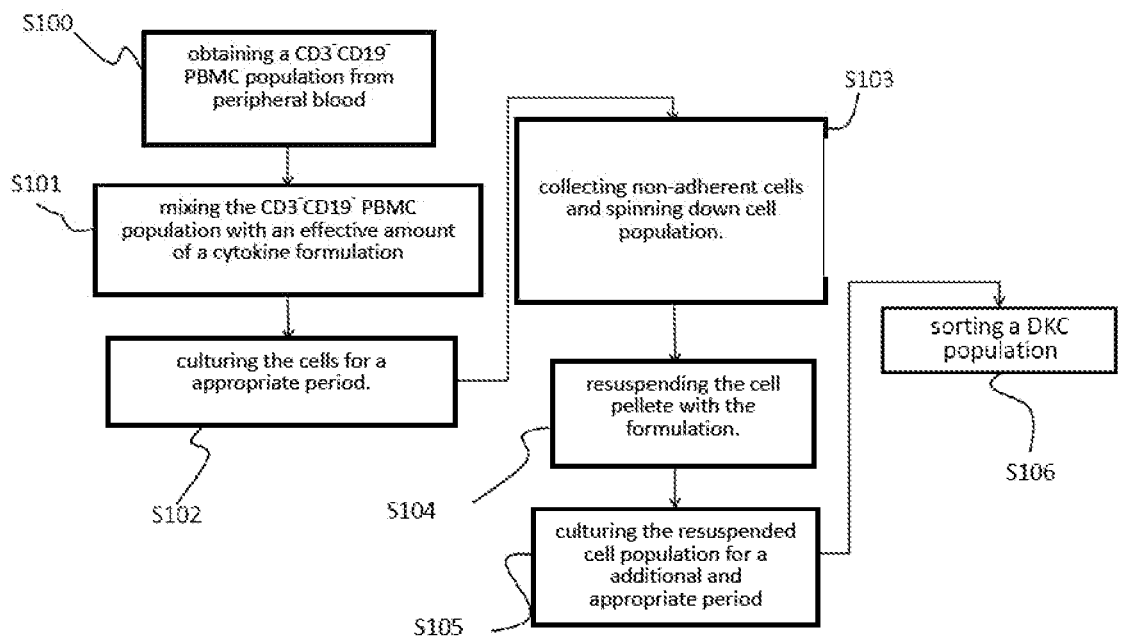
FIG. 3 is flow diagram showing a method according to an embodiment of the present invention for cultivating dendritic killer cells.
Figure 4:
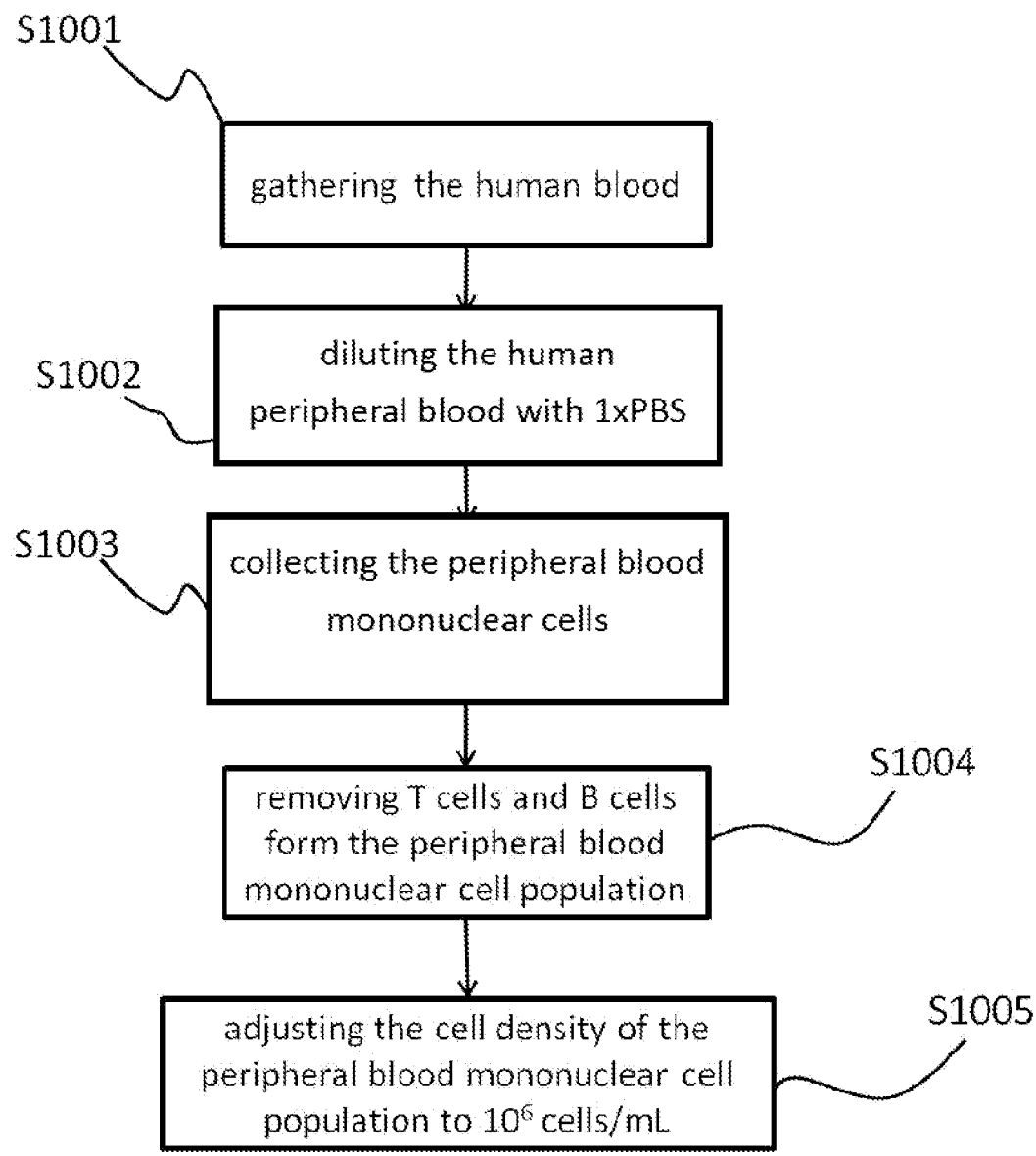
FIG. 4 is flow diagram showing a method according to an embodiment of the present invention for cultivating dendritic killer cells.

In the following, the method disclosed in the present invention for cultivating dendritic killer cells will be further illustrated through FIG. 3 and FIG. 4. FIG. 3 and FIG. 4 are both flow diagrams showing a method according to an embodiment of the present invention for cultivating dendritic killer cells.

Please refer to FIG. 3; step S100 of obtaining a peripheral blood mononuclear cell population from human blood is performed at first. And then, step S101 of adding an effective amount of a formulation to mix with the peripheral blood mononuclear cell population is performed. Preferably, the formulation comprises at least one cytokine and the cytokine is Interleukin-15 (hereafter "IL-15"). The following step S102 is to place the peripheral blood mononuclear cell population for a first appropriate period.

In an embodiment of the present invention, the formulation further comprises another cytokine, and the abovementioned cytokine is Interleukin-12 (hereafter "IL-12"). Preferably, the concentration of IL-15 has a value greater than 1 ng/mL. Furthermore, the concentration of IL-15 is 10 ng/mL, and the concentration of IL-12 has a value between 0.5~20 ng/mL.

Preferably, the first appropriate period means that IL-15 and the peripheral blood mononuclear cell population are both put into a media for a period to let cell proliferation process. Preferably, the first appropriate period is from the third day to the seventh day after starting the abovementioned cultivating step.

After placing for the first appropriate period, step S103 of collecting non-adherent cells is performed at first. A first precipitation is then obtained by treating the non-adherent cells in step S104. The first precipitation will be re-suspended in step S104 by using the abovementioned formulation (IL-15 and IL-12).

The following step S105 is to place the re-suspended first precipitation for a second appropriate period. After placing for the second appropriate period, a dendritic killer cell population will be sorted in step S106. Preferably, the second appropriate period is from the third day to the fourth day after re-suspending the first precipitation by the formulation. Preferably, the step S106 is performed by a flow cytometer, however, the present invention is not limited thereto. Furthermore, the step S106 can also be performed after the step S102.

It is noted that the first appropriate period or the second appropriate period are both the preferred embodiment, however, the present invention is not limited thereto. That is, the steps S103~S105 can be performed on the fourth day after cultivating, and the step S106 can be performed on the tenth day after cultivating. Furthermore, the steps S103~S104 can be repeatedly performed after the step S105. That is, no-adherent cells will be collected again and further treated to obtain a second precipitation. And then, the second precipitation is re-suspended by the formulation and placed for a third appropriate period. Finally the counts of the dendritic killer cells will be expanded to an expect value by repeating the abovementioned steps.

Please refer to FIG. 4; the step S100 further comprises the following steps. At first, the human blood is collected in step S1001, and 2-fold diluted by PBS in step S1002. The peripheral blood mononuclear cell population is then sorted from the human blood in step S1003. T cells and B cells are removed from the peripheral blood mononuclear cell population in step S1004. The eventual step S1005 is to adjust cell density into $1 \times 10^6$ cells/ml. Preferably, the human blood is whole blood and the step S1003 is performed by flow cytometry or Ficoll-Paque density gradient centrifugation.

It is needed to be further illustrated that the step S1004 can be performed by flow cytometry or Ficoll-Paque density gradient centrifugation. To take the flow cytometry as an example, the step S1004 further comprises the following steps. At first, the step of detecting the existence of T cell surface marker and B cell surface markers of the peripheral blood mononuclear cell population. Preferably, B cell surface markers are intended to refer to a cell surface marker presented on the surface of B cell, such as CD 19, and T cell surface markers are intended to refer to a cell surface marker presented on the surface of T cell, such as CD3. Therefore, the following step will remove the cells with the B cell surface markers and T cell surface markers. That is, the remaining are the cells with surface markers of CD3$^-$ and CD19$^-$.

The present invention can further utilize a magnetic beads sorting technology to perform the step S1004. At first, anti-CD3-biotin and anti-CD19-biotin are added to react with the peripheral blood mononuclear cell population. And then, magnetic beads covered by anti-biotin are added into the abovementioned mixture and let the mixture pass through a column with a magnetic field. Therefore, T cells and B cells caught by the antibody and the magnetic beads will be stayed in the column. The peripheral blood mononuclear cell population without T cells and B cells will be obtained.

According to the abovementioned, the formulation disclosed in the present invention comprises cytokine(s), and the cytokine(s) means only IL-15, or IL-15 and IL-12. However, the present invention is not limited thereto. However, it is to be noted that the formulation with only IL-15 can achieve an expected and good result. That is, the addition of IL-12 can further enhance the effect, but IL-12 is not necessary. And further, IL-12 cannot use solely.

Please refer from FIG. 5A to FIG. 5D; FIG. 5A to FIG. 5D are diagrams showing the results of adding media (negative control), IL-12, IL-15 and IL-15+IL-12 to cultivate dendritic killer cells for three days.

Figure 5A:
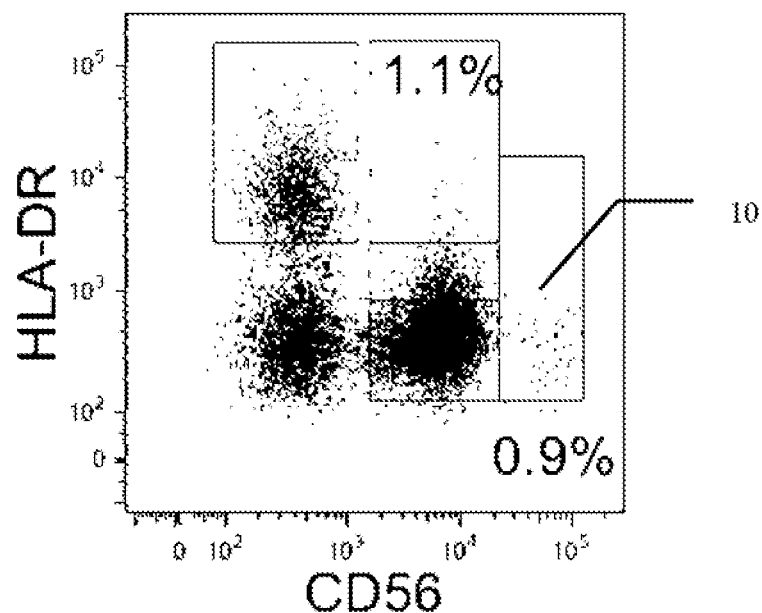
FIG. 5A to FIG. 5D are diagrams showing the results of adding media, IL-12, IL-15 and IL-15+IL-12 to cultivate dendritic killer cells for three days.
Figure 5B:
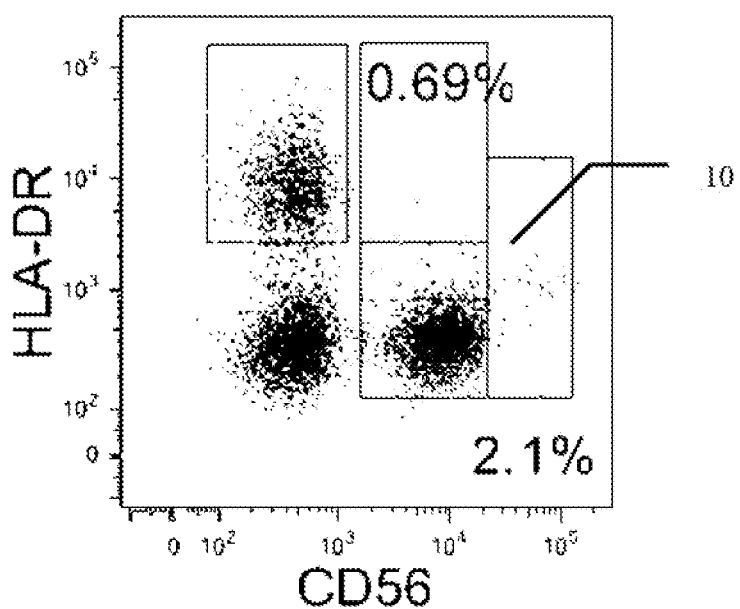
Figure 5C:
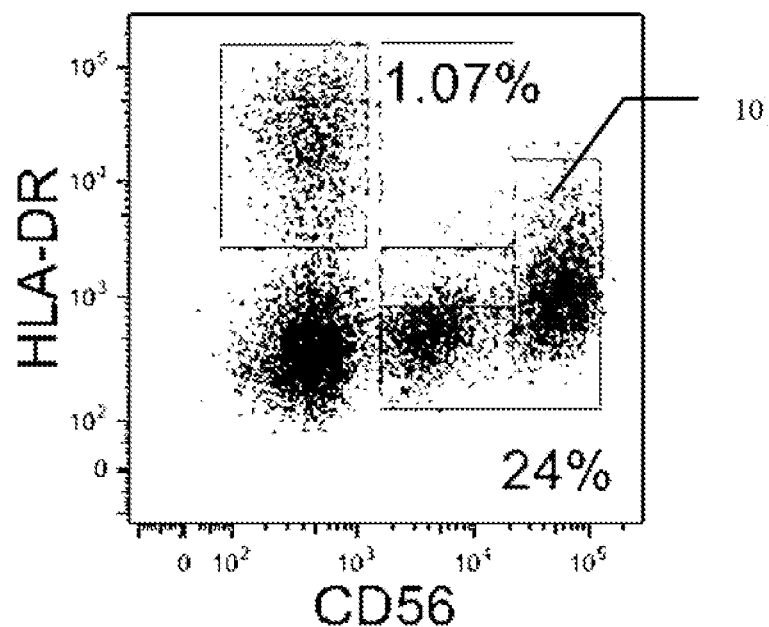
Figure 5D:
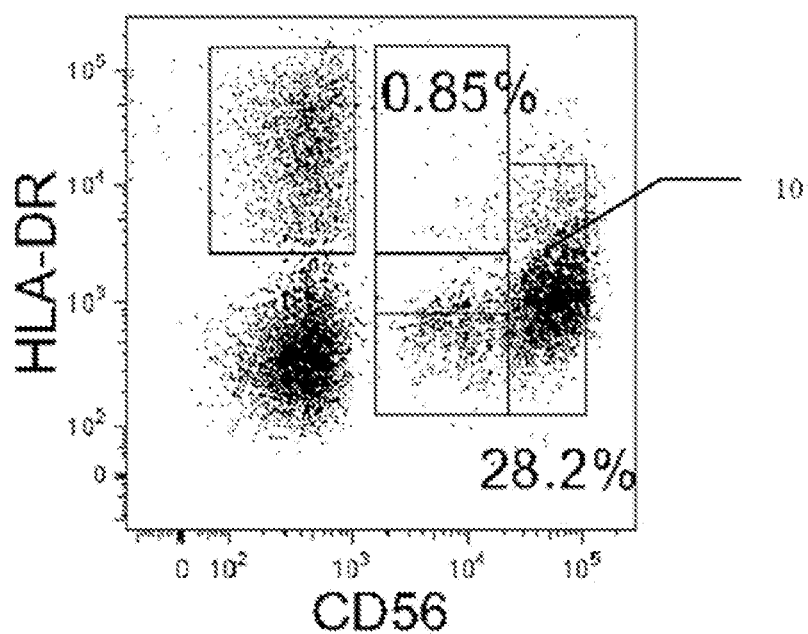

At first, please refer to the most right block of FIGS. 5A-5D, they shows the counts of the DKC 10. As shown in FIG. 5A, there is only media therein and the counts of the DKC increase only 0.9%. As shown in FIG. 5B, there is 50 ng/mL IL-12 added therein and the counts of the DKC increase only 2.1%. As shown in FIG. 5C, there is 10 ng/mL IL-15 added therein and the counts of the DKC increase 24%. As shown in FIG. 5D, there are both 10 ng/mL IL-15 and 1.8 ng/mL IL-12 added therein and the counts of the DKC increase 28.2%. Therefore, the experimental results clearly point out that the formulation with only IL-15 can achieve an expected effect. That is, the present invention is not limited to use the formulation with both IL-12 and IL-15, and the addition of IL-12 is to enhance the abovementioned effect.

Preferably, the concentration of IL-15 is 10 ng/mL. However, it is enough that the concentration of IL-15 has a value greater than 1 ng/mL. Preferably, the concentration of IL-12 has a value between 0.5~20 ng/mL.

Figure 6A:
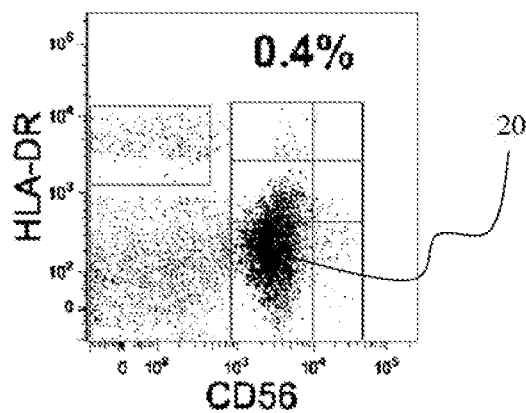
FIG. 6A to FIG. 6C are diagrams showing the results of detecting dendritic killer cells by a flow cytometer before cultivating, after cultivating for three days and after cultivating for seven days.
Figure 6B:
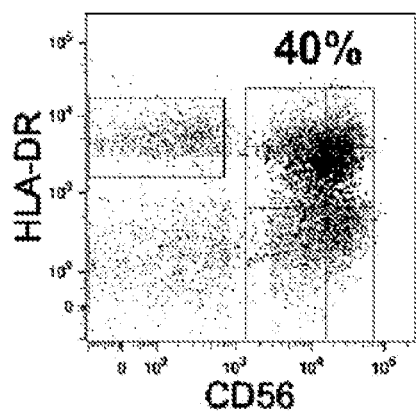
Figure 6C:
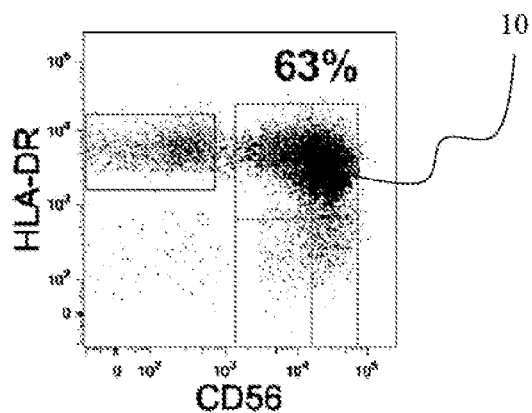
Figure 7:
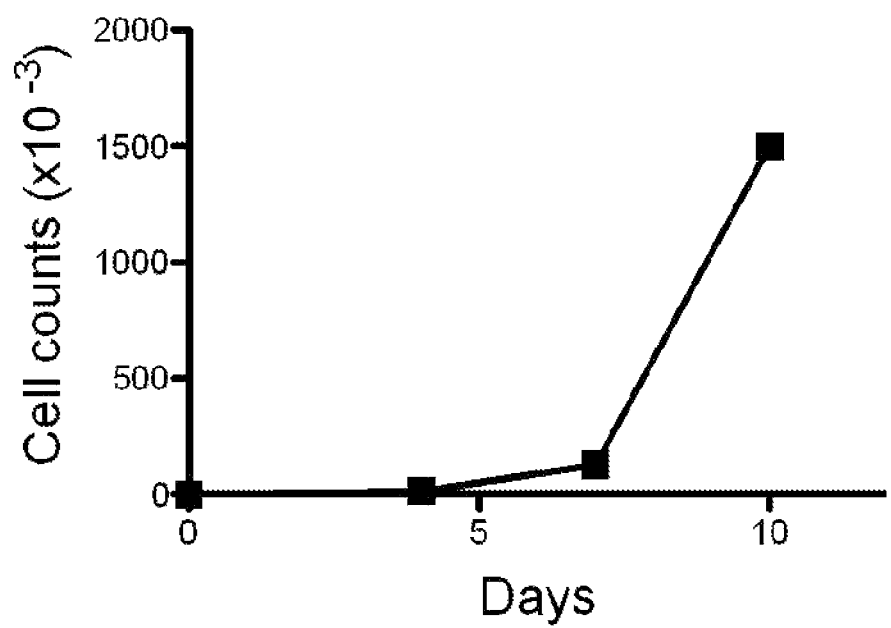
FIG. 7 is diagram showing the relation between the cultivating days and the counts of dendritic killer cells.

The following experimental results will be illustrated by referring from FIG. 6A to FIG. 6C and FIG. 7. FIG. 6A to FIG. 6C are diagrams showing the results of detecting dendritic killer cells by a flow cytometer before cultivating, after cultivating for three days and after cultivating for seven days, and FIG. 7 is diagram showing the relation between the cultivating days and the counts of dendritic killer cells. As shown in FIG. 6A, the counts of the cells which have natural killer cell surface marker (CD56$^+$) and dendritic Cell surface marker (HLA-DR) are much fewer. And further, the cells 20 positioned at the central portion of FIG. 6A are natural killer cells which have the surface marker of CD 56 but not HLA-DR.

As shown in FIG. 6B and FIG. 6C, the cells 20 will move to the upper right corner of the figures as the cultivating time increase. That is, the cells will transfer to the DKC 10 which has both natural killer cell surface marker and dendritic Cell surface marker. Therefore, it can be proved that the formulation and the method disclosed in the present invention can expand the counts of the DKC and further let natural killer cells transfer to DKC.

Please refer to FIG. 7, as the cultivating time increase, the counts of the DKC also increase. And further, the counts of the DKC can be 200-fold to 400-fold expanded after cultivating for seven days. That is, the cell counts of the dendritic killer cell population, which is cultivated by the formulation and method disclosed in the present invention, have a 200-fold to 400-fold higher value than that of human blood.

To sum up, although DKC plays an important role in immunoreactions, the content of the DKC in the human body is very rare. Therefore, the trace DKC of the human blood can be expanded from 200-fold to 400-fold by the formulation and method disclosed in the present invention. Moreover, the human blood used in the present invention is collected from a cancer patient. As shown in FIG. 1, the counts of the DKC existed in the cancer patient are much fewer, that is, the present invention can cultivate and expand the DKC to an expected counts even if the original counts of the DKC are fewer and fewer.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method for cultivating dendritic killer cells, comprising the following steps:
    (a) obtaining a peripheral blood mononuclear cell population from human blood;
    (b) adding an effective amount of IL-15 and IL-12 to the peripheral blood mononuclear cell population, to make the concentration of IL-15 greater than 1 ng/mL, and to make the concentration of IL-12 between 0.5-20 ng/mL;
    (c) culturing the cells for a first appropriate period: and
    (d) sorting the dendritic killer cells, wherein the dendritic killer cells are cells with the surface marker HLA-G$^-$ CD14$^-$ CD19$^-$ CD3$^-$ CD56$^+$ HLA-DR$^+$.

2. The method according to claim 1, wherein the concentration of IL-15 is 10 ng/mL.

3. The method according to claim 1, wherein between said step (c) and said step (d), said method further comprises the following steps:
   (z1) collecting non-adherent cells;
   (z2) spinning down the non-adherent cells to obtain a precipitation;
   (z3) re-suspending said precipitation in a formulation comprising an effective amount of IL-15 and IL-12; and
   (z4) culturing the re-suspended precipitation for a second appropriate period.

4. The method according to claim 1 wherein between the step (a) and the step (b), the method further comprises the following step:
   (x) depleting $CD3^+$ cells and $CD19^+$ cells from the human peripheral blood mononuclear cells.

5. The method according to claim 1, wherein after the step (d), the number of the dendritic killer cell population increases 200-fold to 400-fold compared to its number in step (a).

6. The method according to claim 1, wherein the step (a) further comprises the following steps:
   (a1) collecting the human blood;
   (a2) sorting the peripheral blood mononuclear cell population from the human blood; and
   (a3) removing T cells and B cells from the peripheral blood mononuclear cell population.

7. The method according to claim 6, wherein the human blood in the step (a1) is obtained from a cancer patient.

8. The method according to claim 7, wherein the cancer patient suffers from a cancer, and the cancer can be selected from a group consisting of squamous cell carcinoma, lobular carcinoma in situ, liver cancer, nasopharyngeal carcinoma, lung cancer, bone cancer, pancreatic cancer, skin cancer, head and neck cancers, malignant melanoma, cervical cancer, ovarian cancer, colon cancer, anal cancer, stomach cancer, breast cancer, testicular cancer, fallopian tube cancer, endometrial cancer, cervical cancer, vaginal cancer, vulvar cancer, non-Hodgkin lymphoma, Hodgkin lymphoma, esophageal cancer, thyroid cancer, adrenal cancer, cancers of mesothelial and soft tissue, urethra cancer, cancer of penis, prostate cancer, acute leukemia, chronic leukemia, lymphomas, bladder cancer, ureteral cancer, renal cell carcinoma, urothelial carcinoma, cancer of central nervous system, primary central nervous system lymphoma, glioma, pituitary tumor, Kaposi's sarcoma, squamous cell cancer and their metastasis.

9. A method of obtaining an enriched population of human dendritic killer cells, the method comprising:
   (a) obtaining human peripheral blood mononuclear cells (PBMCs), and in line 7 0.5~20;
   (b) depleting $CD3^+$ cells and $CD19^+$ cells from the human peripheral blood mononuclear cells to obtain human $CD3^-CD19^-$ PBMCs:
   (c) culturing the human $CD3^-CD19^-$PBMCs in a medium containing IL-15 and 0.5-20 ng/mL IL-12;
   (d) isolating non-adherent cells to obtain a dendritic killer cell-enriched cell population; and
   (e) sorting the dendritic killer cells from the dendriitic killer cell-enriched cell population, wherein the dendritic killer cells are cells with the surface marker HLA-$G^-$ $CD14^-$ $CD19^-$ $CD3^-$ $CD56^+$ $HLA-DR^+$.

10. The method according to claim 9, wherein the concentration of IL-15 is 10 ng/mL.

11. The method according to claim 9, wherein the human peripheral blood mononuclear cells are collected from a cancer patient.

* * * * *